US012491070B2

(12) United States Patent
O'Connor et al.

(10) Patent No.: US 12,491,070 B2
(45) Date of Patent: Dec. 9, 2025

(54) STENT-VALVE DELIVERY SYSTEM

(71) Applicant: BOSTON SCIENTIFIC SCIMED, INC., Maple Grove, MN (US)

(72) Inventors: Tim O'Connor, Galway (IE); Sean Shanley, Galway (IE); John Lardner, Galway (IE); Declan Loughnane, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 696 days.

(21) Appl. No.: 17/954,657

(22) Filed: Sep. 28, 2022

(65) Prior Publication Data

US 2023/0093867 A1 Mar. 30, 2023

Related U.S. Application Data

(60) Provisional application No. 63/249,689, filed on Sep. 29, 2021.

(51) Int. Cl.
*A61F 2/24* (2006.01)
*A61M 25/01* (2006.01)

(52) U.S. Cl.
CPC .......... *A61F 2/2436* (2013.01); *A61F 2/2418* (2013.01); *A61M 25/0108* (2013.01)

(58) Field of Classification Search
CPC ...... A61F 2/2436; A61F 2/2433; A61F 2/243; A61F 2/9661; A61F 2/9662; A61F 2/962; A61F 2/9522
See application file for complete search history.

(56) References Cited

U.S. PATENT DOCUMENTS 4,641,657 A * 2/1987 Ellis .......................... A61B 8/12
606/1
8,647,381 B2 * 2/2014 Essinger ............... A61F 2/2436
623/1.24

(Continued)

FOREIGN PATENT DOCUMENTS

EP 3583918 A1 12/2019
JP 2013524934 A 6/2013

(Continued)

OTHER PUBLICATIONS

International Search Report and Written Opinion dated Jan. 11, 2023 for International Application No. PCT/US2022/045006.

*Primary Examiner* — Alvin J Stewart
(74) *Attorney, Agent, or Firm* — Seager, Tufte & Wickhem LLP

(57) ABSTRACT

A delivery system for delivering a stent-valve may include an inner shaft including a distal tip, a stent-valve crimped onto the inner shaft, a distal sheath disposed over at least a lower portion of the stent-valve, and a proximal sheath disposed over at least an upper portion of the stent-valve. The distal sheath has a proximal free end with an angled proximal edge defining a short side and a long side of the distal sheath. The proximal sheath is actuatable independently from the distal sheath, and moveable proximally to release the upper portion of the stent-valve. The distal sheath is moveable distally to release the lower portion of the stent-valve. The angled proximal edge releases a first side of the lower portion of the stent-valve before an opposite second side.

20 Claims, 15 Drawing Sheets

(56) References Cited

U.S. PATENT DOCUMENTS

| | | | |
|---|---|---|---|
| 9,839,515 | B2 | 12/2017 | Von Segesser et al. |
| 10,376,359 | B2 * | 8/2019 | Essinger ............... A61F 2/2412 |
| 10,398,548 | B2 * | 9/2019 | Willard ............. A61M 25/0074 |
| 10,524,908 | B2 * | 1/2020 | Peterson ................... A61F 2/95 |
| 11,007,074 | B2 * | 5/2021 | Bueche ................... A61F 2/966 |
| 12,121,460 | B2 * | 10/2024 | Bueche ................... A61F 2/966 |
| 2006/0085057 | A1 | 4/2006 | George et al. |
| 2008/0147182 | A1 * | 6/2008 | Righini ................... A61F 2/243 623/2.11 |
| 2010/0100167 | A1 * | 4/2010 | Bortlein .................... A61F 2/95 623/1.11 |
| 2010/0268315 | A1 * | 10/2010 | Glynn ....................... A61F 2/95 623/1.11 |
| 2013/0274870 | A1 * | 10/2013 | Lombardi ............. A61F 2/2427 623/2.11 |
| 2013/0297012 | A1 * | 11/2013 | Willard ................. A61F 2/2427 623/2.11 |

FOREIGN PATENT DOCUMENTS

| | | | | |
|---|---|---|---|---|
| JP | 2016165493 | A | 9/2016 | |
| WO | WO-2011133271 | A1 * | 10/2011 | ............. A61F 2/243 |

* cited by examiner

STENT-VALVE DELIVERY SYSTEM

CROSS-REFERENCE TO RELATED APPLICATIONS

This application claims the benefit of priority of U.S. Provisional Application No. 63/249,689 filed Sep. 29, 2021, the entire disclosure of which is hereby incorporated by reference.

TECHNICAL FIELD

The disclosure pertains to medical devices and more particularly to delivery systems for replacement heart valves, and methods for using such medical devices and systems.

BACKGROUND

A wide variety of medical devices have been developed for medical use including, for example, medical devices utilized to replace heart valves. Heart function can be significantly impaired when a heart valve is not functioning properly. When the heart valve is unable to close properly, the blood within a heart chamber can regurgitate, or leak backwards through the valve. Valve regurgitation may be treated by replacing or repairing a diseased valve, such as an aortic valve. Surgical valve replacement is one method for treating the diseased valve, however this requires invasive surgical openings into the chest cavity and arresting of the patient's heart and cardiopulmonary bypass. Minimally invasive methods of treatment, such as transcatheter aortic valve implantation (TAVI) or transcatheter aortic valve replacement (TAVR), generally involve the use of delivery catheters that are delivered through arterial passageways or other anatomical routes into the heart to replace the diseased valve with an implantable prosthetic heart valve.

In some cases, embolization of a prosthetic heart valve occurs, often due to movement of the prosthetic valve at or soon after expansion during deployment. Of the known delivery systems and methods for implanting a prosthetic heart valve, each has certain advantages and disadvantages. There is an ongoing need to provide alternative delivery systems as well as alternative methods for manufacturing and using the medical devices.

SUMMARY

This disclosure provides design, material, manufacturing method, and use alternatives for medical devices. An example delivery system configured to deliver a stent-valve comprises an inner shaft including a distal tip, a stent-valve crimped onto the inner shaft, the stent-valve including an upper portion, a lower portion, and a valve, a distal sheath disposed over at least the lower portion of the stent-valve, the distal sheath having a distal end coupled to the distal tip and a proximal free end having an angled proximal edge defining a short side and a long side of the distal sheath, and a proximal sheath disposed over at least the upper portion of the stent-valve, wherein the proximal sheath is actuatable independently from the distal sheath, and moveable proximally to release the upper portion of the stent-valve, wherein the distal sheath is moveable distally to release the lower portion of the stent-valve, wherein the angled proximal edge releases a first side of the lower portion of the stent-valve before an opposite second side.

Alternatively or additionally to the embodiment above, the angled proximal edge on the distal sheath is angled 10 degrees to 70 degrees relative to a transverse axis of the distal sheath.

Alternatively or additionally to any of the embodiments above, the angled proximal edge has a 10-degree to 20-degree angle.

Alternatively or additionally to any of the embodiments above, the delivery system further comprises a marker indicating a position of the long side of the distal sheath.

Alternatively or additionally to any of the embodiments above, the marker is a radiopaque marker on the distal sheath along the long side.

Alternatively or additionally to any of the embodiments above, the marker is a radiopaque marker on the lower portion of the stent-valve.

Alternatively or additionally to any of the embodiments above, the lower portion of the stent-valve includes a plurality of lower crowns, wherein the long side includes a proximal extension configured to cover 1-5 of the lower crowns while the remaining lower crowns are released.

Alternatively or additionally to any of the embodiments above, the proximal sheath has a distal free end with an angled distal edge, wherein when the proximal sheath is moved proximally, the angled distal edge releases a first side of the upper portion of the stent-valve before an opposite second side.

Alternatively or additionally to any of the embodiments above, the upper portion of the stent-valve includes a plurality of arches and a plurality of upper crowns, wherein a distal end of the proximal sheath extends over the plurality of arches and the plurality of upper crowns.

Alternatively or additionally to any of the embodiments above, the distal sheath includes a polymer sheath and a reinforcement coil, wherein the reinforcement coil extends from the distal end of the distal sheath to a position adjacent the angled proximal edge.

Alternatively or additionally to any of the embodiments above, the distal sheath includes a braid disposed proximal of the reinforcement coil.

Another example delivery system configured to deliver a stent-valve comprises an inner shaft including a distal tip, a stent-valve crimped onto the inner shaft, the stent-valve including a plurality of upper crowns, a plurality of lower crowns, and a valve, a distal sheath disposed over and constraining the lower crowns, the distal sheath having a distal end coupled to the distal tip and a proximal free end having an angled proximal edge angled 5 degrees to 70 degrees relative to a transverse axis of the distal sheath, and a proximal sheath disposed over the upper crowns of the stent-valve, wherein the proximal sheath is actuatable independently from the distal sheath, and moveable proximally to release the upper crowns of the stent-valve, wherein the distal sheath is moveable distally to release the lower crowns of the stent-valve, wherein the angled proximal edge releases the lower crowns incrementally from a first side to a second side of the stent-valve.

Alternatively or additionally to the embodiment above, the angled proximal edge has a 10-degree to 20-degree angle.

Alternatively or additionally to any of the embodiments above, the angled proximal edge of the distal sheath defines a long side and an opposing short side of the distal sheath, the delivery system further comprising a marker indicating a position of the long side of the distal sheath.

Alternatively or additionally to any of the embodiments above, the marker is a radiopaque marker on the distal sheath along the long side.

Alternatively or additionally to any of the embodiments above, the marker is a radiopaque marker on one of the lower crowns positioned under the long side of the distal sheath.

Alternatively or additionally to any of the embodiments above, the long side includes a proximal extension configured to cover 1-5 of the lower crowns while the remaining lower crowns are released.

An example method of delivering a stent-valve comprises inserting a distal tip of a stent-valve delivery system through a patient's aorta and aortic valve, the delivery system including an inner shaft including the distal tip, a stent-valve crimped onto the inner shaft, the stent-valve including an upper portion, a lower portion, and a valve, a distal sheath disposed over at least the lower portion of the stent-valve, the distal sheath having a distal end coupled to the distal tip and a proximal free end having an angled proximal edge defining a short side and a long side, the distal sheath including a radiopaque marker on the long side, and a proximal sheath disposed over at least the upper portion of the stent-valve. The method further comprising aligning the radiopaque marker along an outer curve of the aorta, moving the proximal sheath proximally to release the upper portion of the stent-valve, and moving the distal sheath distally to release the lower portion of the stent-valve, the angled proximal edge releasing a first side of the lower portion of the stent-valve positioned on an inner curve of the aorta, before an opposite second side.

Alternatively or additionally to the embodiment above, moving the distal sheath includes a first stage in which the distal sheath is moved distally to a first position in which a first side of the lower portion of the stent-valve is released while a second side of the lower portion of the stent-valve remains constrained by the distal sheath, and a second stage in which the distal sheath is moved further distally until an entirety of the lower portion of the stent-valve is released from the distal sheath.

Alternatively or additionally to any of the embodiments above, after the first stage, the first side of the lower portion of the stent-valve is allowed to engage a desired portion of the patient's anatomy, and then the second stage is performed to fully release the stent-valve.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
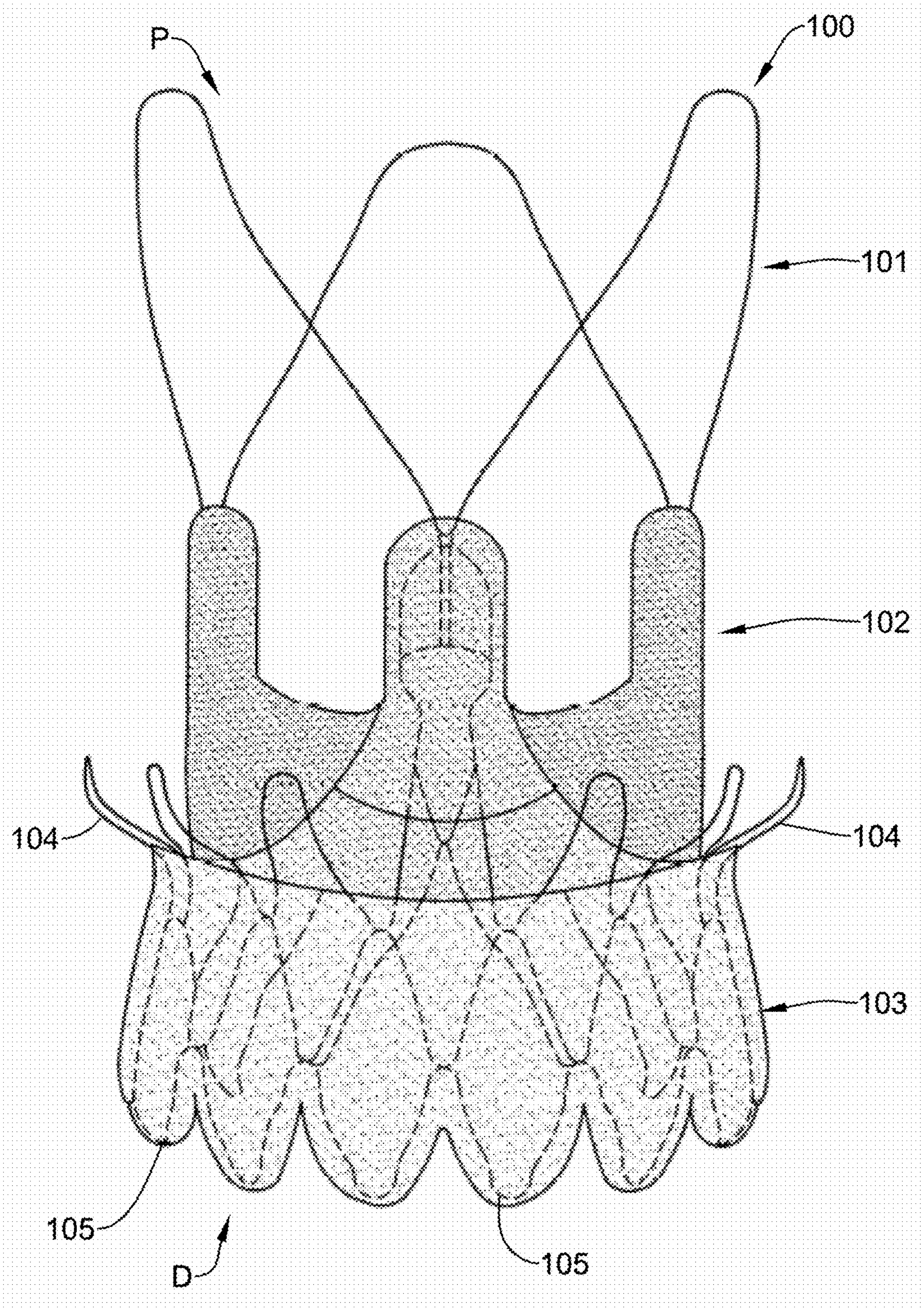
FIG. 1 Prior Art
FIG. 1 illustrates a prior art replacement heart stent-valve.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as “proximal”, “distal”, “advance”, “withdraw”, variants thereof, and the like, may be generally considered with respect to the positioning, direction, and/or operation of various elements relative to a user/operator/manipulator of the device, wherein “proximal” and “withdraw” indicate or refer to closer to or toward the user and “distal” and “advance” indicate or refer to farther from or away from the user. In some instances, the terms “proximal” and “distal” may be arbitrarily assigned in an effort to facilitate understanding of the disclosure, and such instances will be readily apparent to the skilled artisan. Other relative terms, such as “upstream”, “downstream”, “inflow”, and “outflow” refer to a direction of fluid flow within a lumen, such as a body lumen, a blood vessel, or within a device.

The term “extent” may be understood to mean a greatest measurement of a stated or identified dimension, unless the extent or dimension in question is preceded by or identified as a “minimum”, which may be understood to mean a smallest measurement of the stated or identified dimension. For example, “outer extent” may be understood to mean a maximum outer dimension, “radial extent” may be understood to mean a maximum radial dimension, “longitudinal extent” may be understood to mean a maximum longitudinal dimension, etc. Each instance of an “extent” may be different (e.g., axial, longitudinal, lateral, radial, circumferential, etc.) and will be apparent to the skilled person from the context of the individual usage. Generally, an “extent” may be considered a greatest possible dimension measured according to the intended usage, while a “minimum extent” may be considered a smallest possible dimension measured according to the intended usage. In some instances, an “extent” may generally be measured orthogonally within a plane and/or cross-section, but may be, as will be apparent from the particular context, measured differently—such as, but not limited to, angularly, radially, circumferentially (e.g., along an arc), etc.

The terms “monolithic” and “unitary” shall generally refer to an element or elements made from or consisting of a single structure or base unit/element. A monolithic and/or unitary element shall exclude structure and/or features made by assembling or otherwise joining multiple discrete elements together.

It is noted that references in the specification to “an embodiment”, “some embodiments”, “other embodiments”, etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a “first” element may later be referred to as a “second” element, a “third” element, etc. or may be omitted entirely, and/or a different feature may be referred to as the “first” element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

FIG. 1 illustrates a prior art aortic replacement stent-valve 100. The stent component of the stent-valve 100 includes an upper portion with a plurality of support arches 101 and a plurality of upper anchoring crowns 104, and a lower stent portion 103 that supports a replacement valve 102 which regulates the blood flow between the left ventricle and the aorta. The arches 101 define the proximal (P) or upstream end, and the lower stent portion 103 defines the distal (D) or downstream end. The lower stent portion 103 also includes a plurality of lower crowns 105. The arches 101 and lower stent portion 103 are self-expandable and act as anchoring structures within the native aortic annulus for the valve 102.

In some cases, embolization of the stent-valve 100 may occur after deployment, and may be related to movement of the stent-valve 100 during or soon after expansion during deployment. Conventional delivery systems for delivering prosthetic stent-valves do not allow for any modification or influence of the final stages of release of the stent-valve, once the distal sheath has been moved off of the distal end of the stent-valve. The subsequent expansion of the stent-valve to contact the surrounding anatomy happens very quickly and without operator control.

Figure 2:
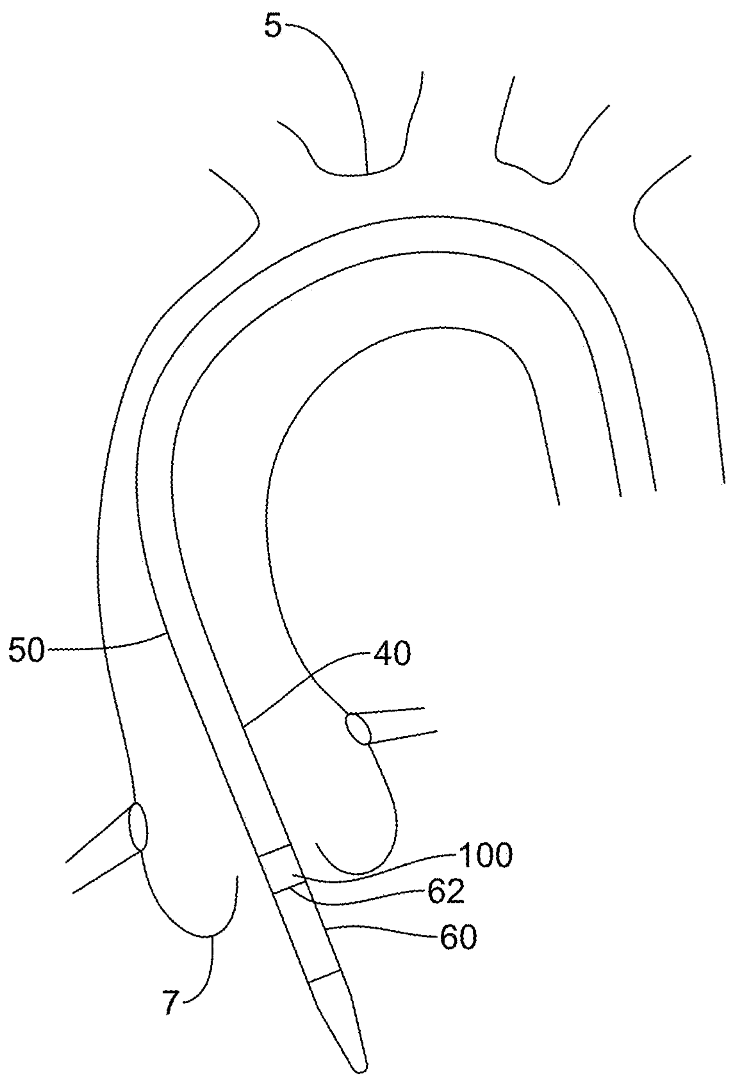
FIG. 2 Prior Art
FIG. 2 illustrates a prior art delivery system disposed within the aortic arch and aortic valve.

FIG. 2 illustrates a conventional stent-valve delivery system 50 during a transfemoral access method. The delivery system 50 is inserted through the femoral artery and vasculature, across the aortic arch 5 and through the aortic valve 7. The delivery system 50 may include a proximal sheath 40 and a distal sheath 60 with a straight proximal edge 62 constraining the stent-valve 100. After the proximal sheath 40 is withdrawn to release the arches 101, the distal sheath 60 is moved distally off the lower stent portion 103, allowing the stent-valve to expand against the aortic valve 7.

Figure 3:
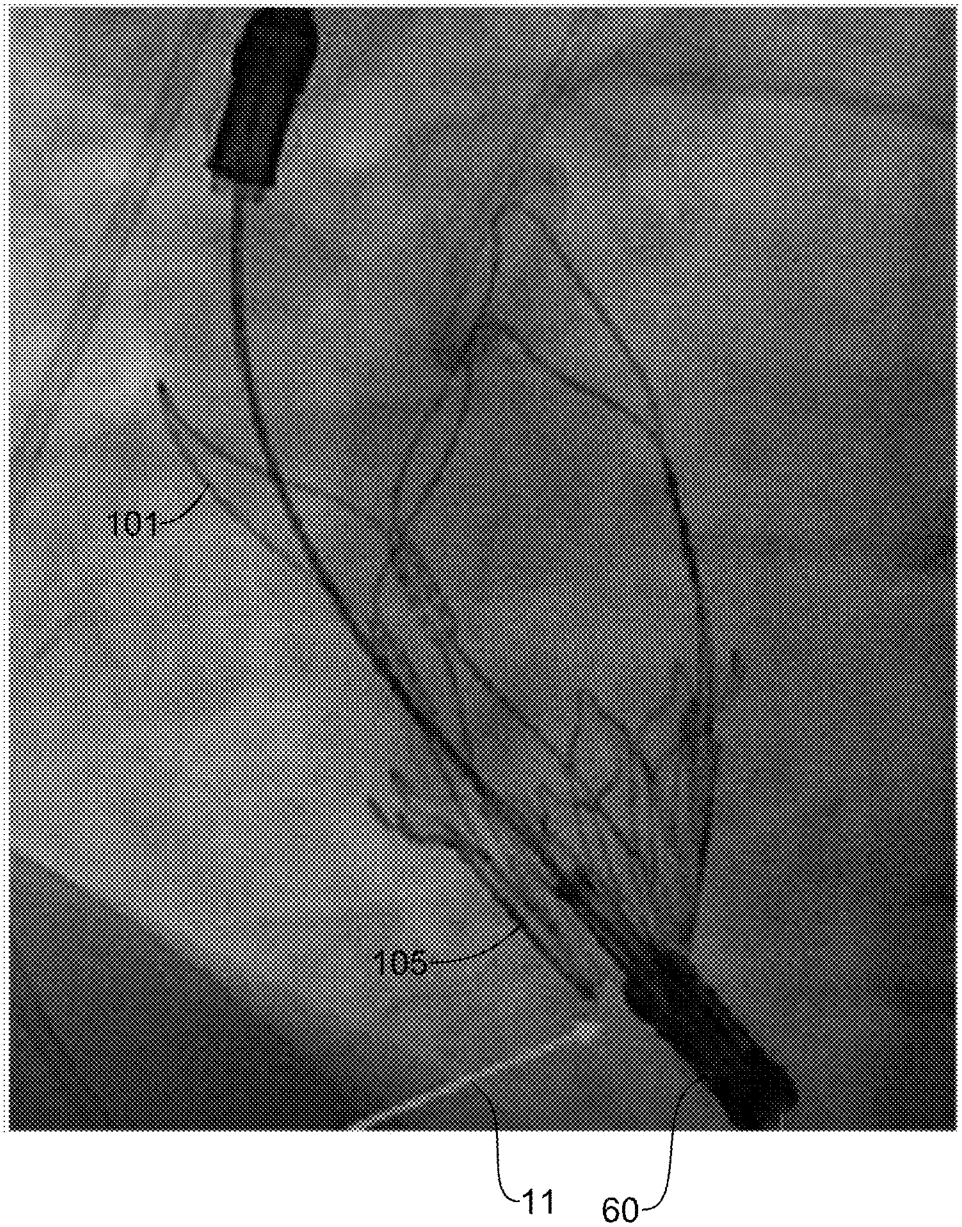
FIG. 3 is a fluoroscopy image showing asymmetrical deployment of a heart-stent valve.

In some cases, particularly in patients with a tighter curve in the aortic arch, when the distal sheath 60 is moved distally off the lower stent portion 103, the tight curve of the aortic arch may cause the entire distal region of the delivery system 50 to curve to match the anatomy. The outer curve and straight proximal edge of the distal sheath 60 may cause a some of the lower crowns 105 along the outer curve to be released before the lower crowns on the opposing side of the stent, as shown at arrow 11 in FIG. 3. This premature asymmetric release of the lower crowns 105 on the outer curve of the delivery system may cause the stent to "jump" or shift as it expands completely, resulting in an undesired deployment location and/or position relative to the aortic valve 7. Withdrawal of the distal sheath 60 and release of the lower crowns 105 using the conventional delivery system results in rapid expansion and seating of the stent-valve, without opportunity for modification of the position of the stent-valve.

A delivery system 250 with strategic shaping of the distal sheath 260 may provide better control for the release of the lower portion of the stent-valve 100 and movement during stent-valve expansion. See FIG. 4. The delivery system 250 may include an inner shaft 210 coupled to a distal tip 215, and an intermediate shaft 212 disposed over the inner shaft 210. A stent holder (not shown) may be coupled to the intermediate shaft 212. The inner shaft 210 may define a guidewire lumen. The stent-valve 100 may be crimped onto the intermediate shaft 212 proximal of the distal tip 215. The distal sheath 260 may have a distal end 262 coupled to the distal tip 215 and a proximal free end 264 having an angled proximal edge 266 defining a short side 261 and a long side 263 of the distal sheath 260. The distal sheath 260 may be disposed over at least the lower stent portion 103.

The angled proximal edge 266 may be angled 10 degrees to 70 degrees relative to a transverse axis of the distal sheath. In other embodiments, the angle may be 10 degrees to 20 degrees. A shallower angle, such as 10 degrees, may achieve simultaneous release of the lower crowns 105, depending on the angle of the anatomy. The type of distal release may be tailored with a particular proximal edge angle. In some embodiments, it may be desired for the distal sheath 260 to constrain at least a first portion or side of the lower stent portion 103 of the stent-valve 100, utilizing an angle of 20 degrees or more. In other embodiments, a symmetrical or simultaneous release of the entire lower stent portion 103 may be desired, utilizing a shallower angle such as 10 degrees.

Figure 5:
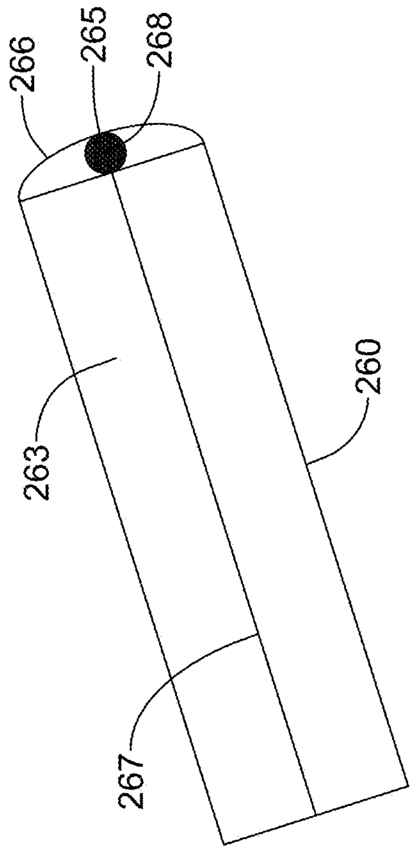
FIG. 5 illustrates the distal sheath of the delivery system of FIG. 4 rotated a quarter turn.

A marker indicating the position of the long side 263 of the distal sheath 260 may be used to aid the user in positioning the delivery system 250 for the desired deployment of the stent-valve. As shown in FIG. 5, the marker may be a line 267 extending partially or completely along the long side 263 of the distal sheath 260. The line 267 may be centered on the long side 263 such that a proximal end of the line 267 is at the proximal tip 265 of the angled proximal edge 266. In other embodiments, the marker may be a dot 268 or other shaped marker indicating the long side 263. The marker may generally be radiopaque to be visible on fluoroscopy, although other markers may be used, in accordance with a desired type of imaging to be used during deployment. Alternatively or in addition to the marker on the distal sheath 260, a marker such as a radiopaque dot or line may be provided on the lower stent portion 103, such as on one of the lower crowns 105.

Figure 4:
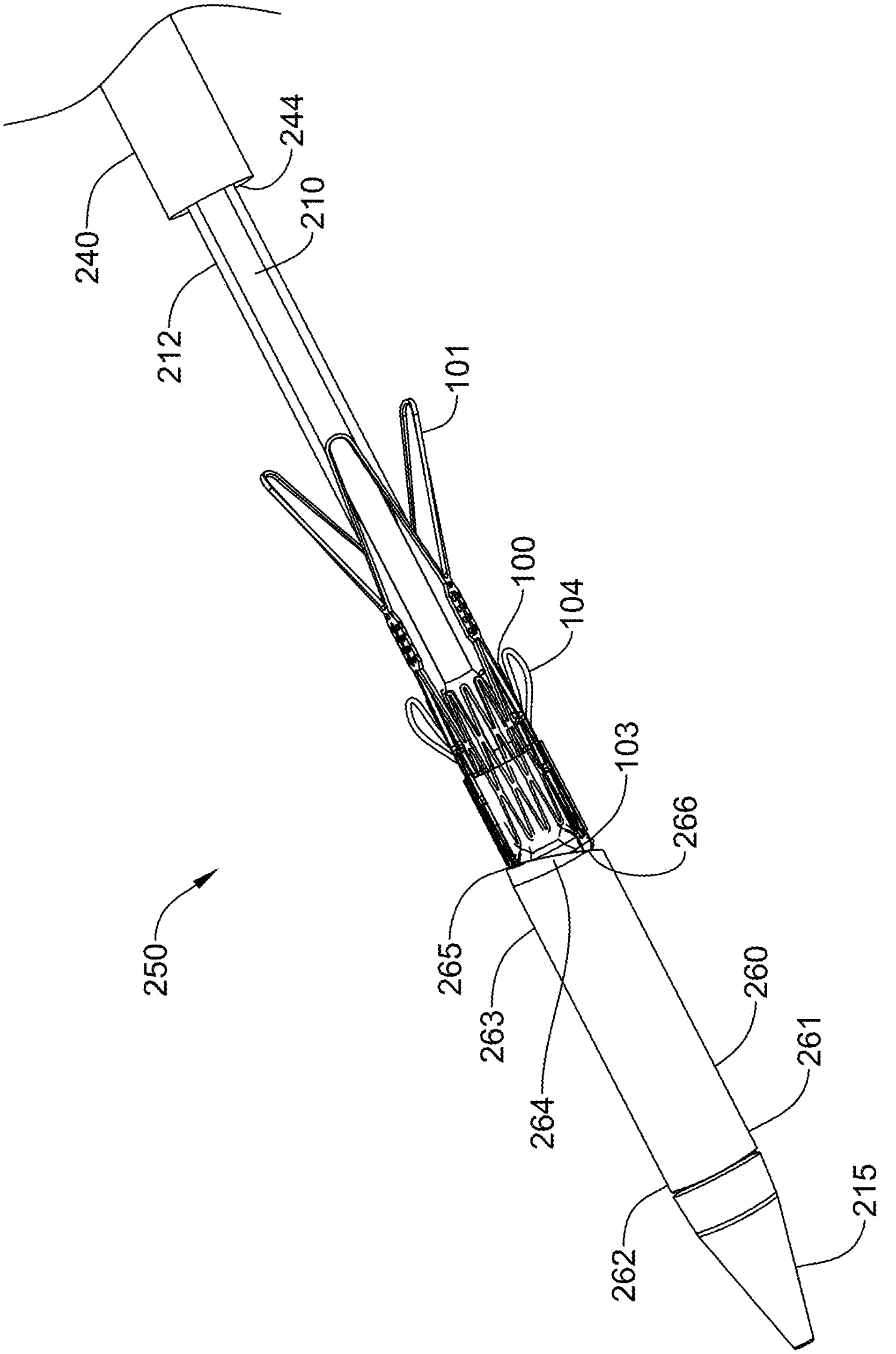
FIG. 4 illustrates an example delivery system with the proximal sheath retracted from the stent-valve.

A proximal sheath 240 may be disposed over at least the upper portion of the stent-valve 100. In some embodiments, the proximal sheath 240 may be disposed over the arches 101 and the upper anchoring crowns 104. The proximal sheath 240 and the distal sheath 260 may meet at the proximal tip 265 of the angled proximal edge 266 of the distal sheath 260. In other embodiments, there may be a gap between the proximal tip 265 of the distal sheath 260 and the distal edge 244 of the proximal sheath 240. The proximal sheath 240 may be actuatable independently from the distal sheath 260, and be moveable proximally relative to the inner shaft 210 and the intermediate shaft 212 to release the upper portion of the stent-valve, including the arches 101 and the upper anchoring crowns 104, as shown in FIG. 4. Upon proximal withdrawal of the proximal sheath 240, the arches 101 and upper anchoring crowns 104 may expand at least partially, but the lower stent portion 103 remains constrained by the distal sheath 260, preventing the stent-valve from becoming secured within the native valve.

Figure 6:
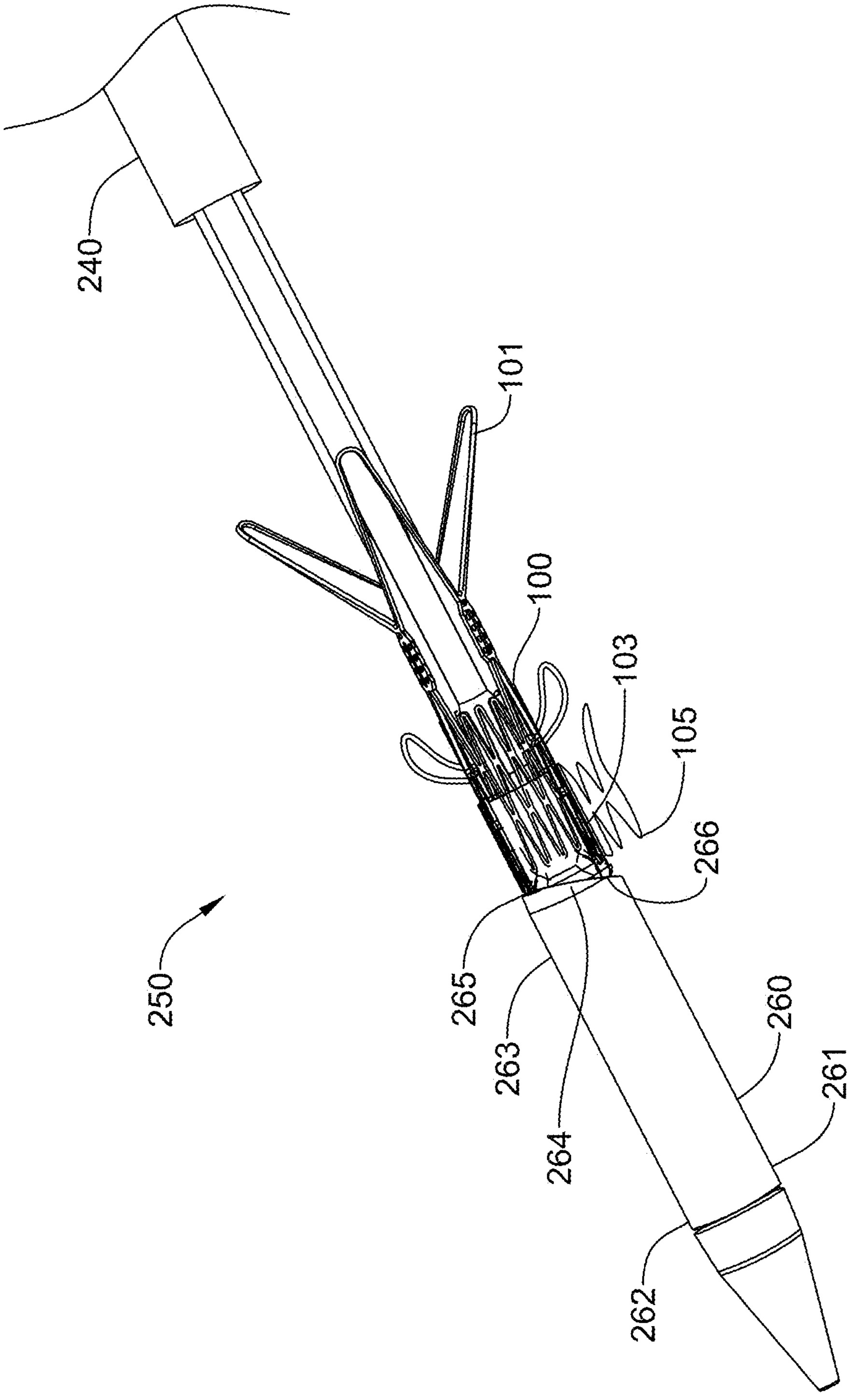
FIG. 6 illustrates the delivery system of FIG. 4 with the distal sheath partially retracted.
Figure 7:
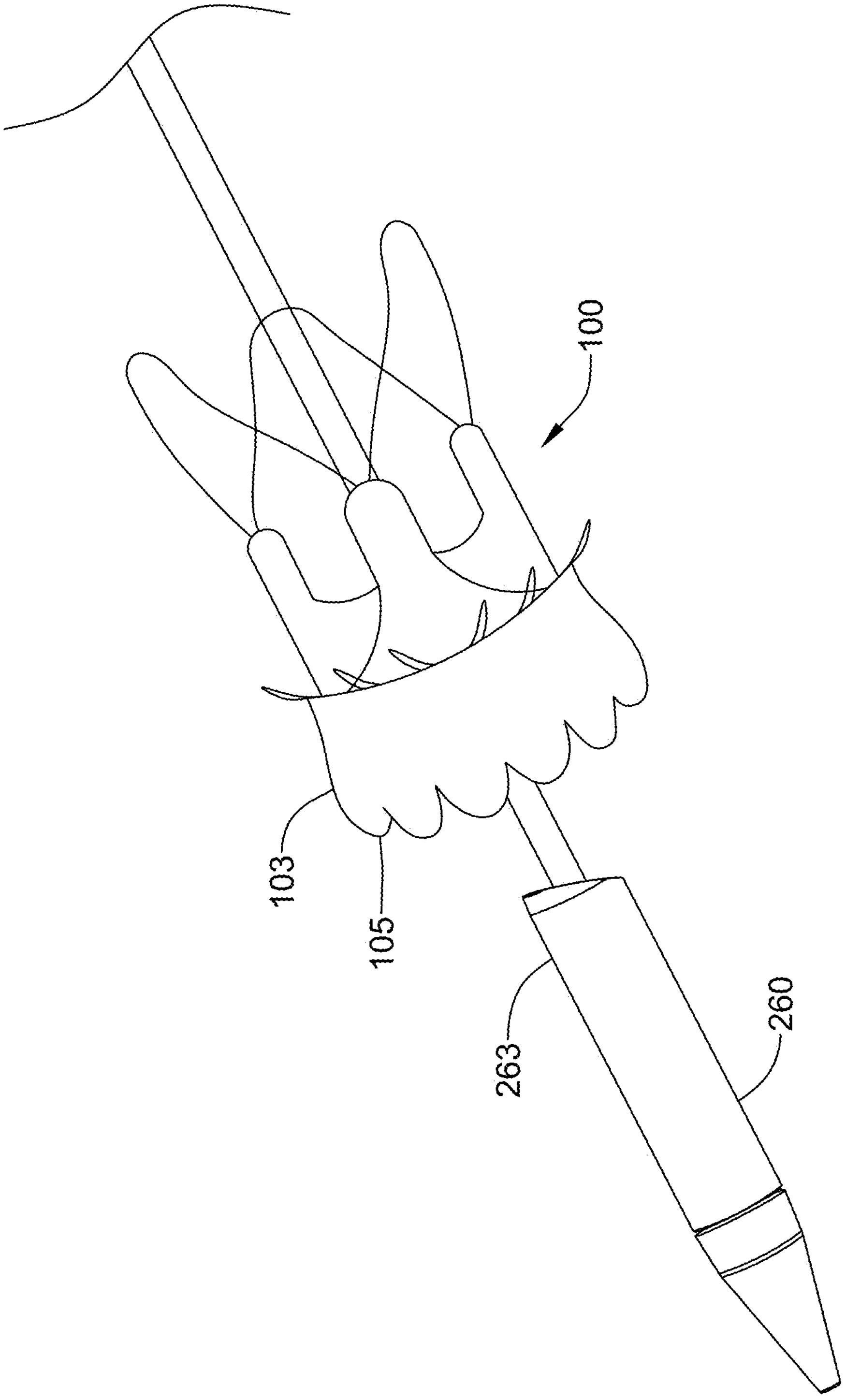
FIG. 7 illustrates the delivery system of FIG. 4 with the distal sheath fully retracted.

The distal sheath 260 may be moveable distally to gradually and incrementally release the lower stent portion 103 of the stent-valve, with the angled proximal edge 266 releasing lower crowns 105 on a first side of the lower stent portion 103 before an opposite second side. As shown in FIG. 6, the short side 261 of the distal sheath 260 releases lower crowns 105 while the long side 263 covers and constrains lower crowns 105 on the opposite side of the lower stent portion 103. When only a few lower crowns 105 have been released, a section of the lower stent portion 103 may expand, however this partial expansion may allow for movement and positioning of the stent-valve within the native valve to achieve the desired position. Once the stent-valve 100 is in the desired position, the distal sheath 260 may be fully withdrawn distally, allowing the long side 263 to uncover the last of the lower crowns 105, at which time the lower stent portion 103 fully expands, as shown in FIG. 7.

Figure 8:
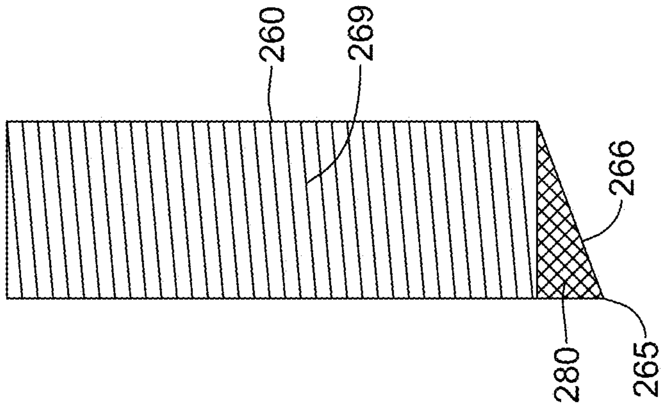
FIG. 8 illustrates the distal sheath of FIG. 4 with a portion of the polymer sheath removed.

In some embodiments, the distal sheath 260 may include a polymer sheath with a reinforcement coil 269 embedded therein. FIG. 8 illustrates the distal sheath 260 with the outer portion of the polymer sheath removed to expose the reinforcement coil 269. The reinforcement coil 269 may extend from the distal end to a position adjacent the angled proximal edge 266. In other embodiments, the distal sheath 260 may include a braid 280 disposed proximal of the reinforcement coil 269. The braid 280 may extend from the reinforcement coil 269 to the proximal tip 265 of the angled proximal edge 266. Alternatively, instead of the reinforcement coil, the distal sheath 260 may include a braid extending along the entirety of the proximal sheath.

Figure 9:
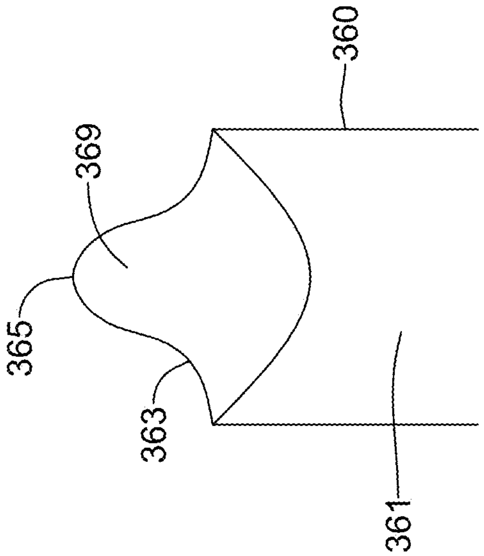
FIG. 9 illustrates another example distal sheath.

In some embodiments, the long side 363 of the distal sheath 360 may include a proximal extension 369 configured to cover a few of the lower crowns 105 while all of the remaining lower crowns are released. As illustrated in FIG. 9, the proximal extension 369 may be a rounded projection defining the proximal tip 365 of the long side 363 of the distal sheath 360. The proximal extension 369 may be directly opposite a lowest point on the short side 361 of the distal sheath 360. The proximal extension 369 may be sized to cover and retain 1-5 lower crowns 105. By strategically shaping the distal sheath 360 leading edge, the final release can be delayed so that the stent-valve is still secured to the delivery system until the lower stent portion 103 is expanded and apposed against the anatomy, reducing the risk of valve migration during release.

Figure 10:
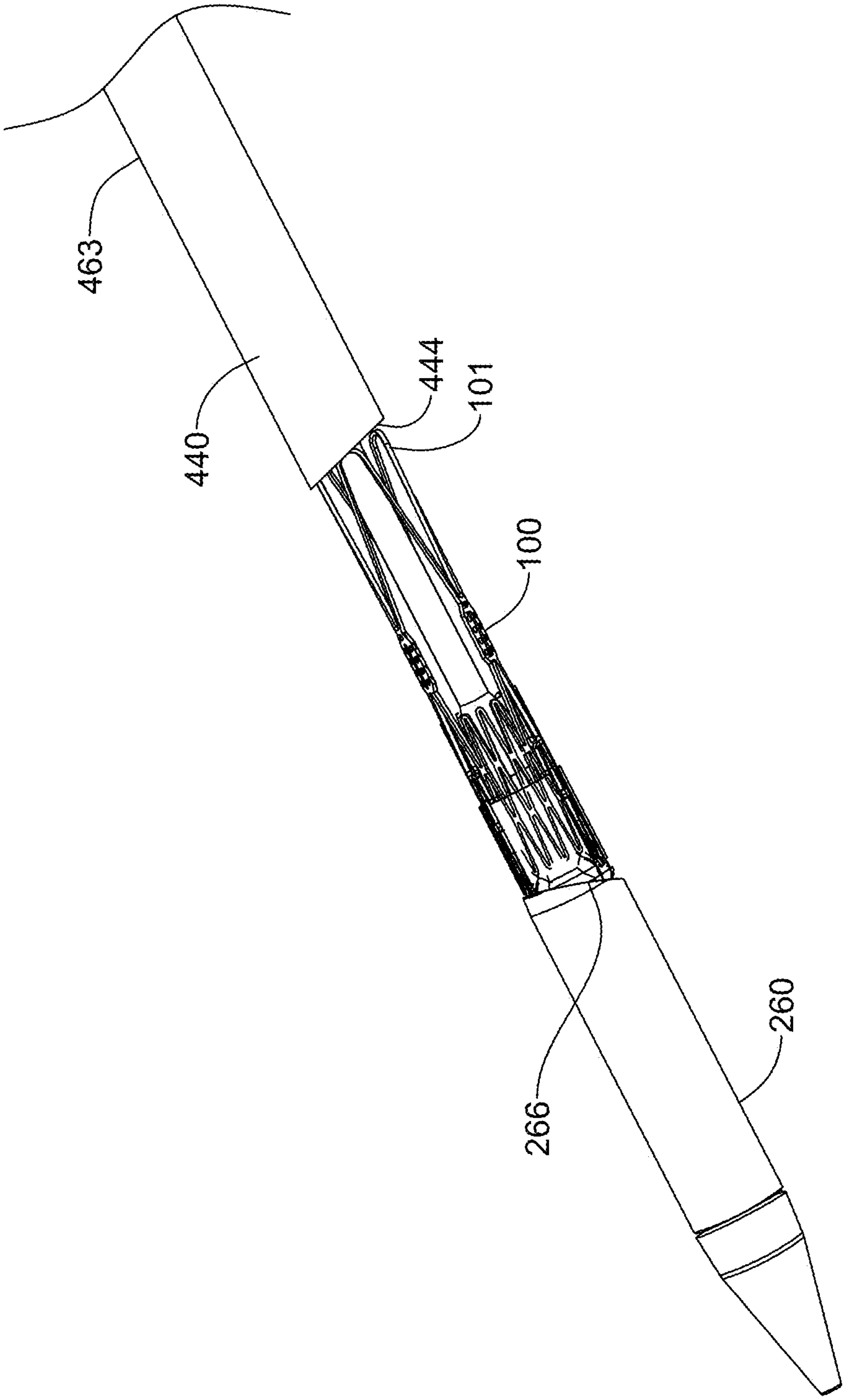
FIG. 10 illustrates another example proximal sheath disposed on the delivery system.

FIG. 10 illustrates an embodiment of proximal sheath 440 with a distal free end having an angled distal edge 444. When the proximal sheath 440 is moved proximally, the angled distal edge 444 releases a first side of the upper portion of the stent-valve 100 before an opposite second side. In the illustrated embodiment, the angled distal edge 444 is angled in an opposite direction from the angled proximal edge 266. With the delivery system inserted so the long side 463 of the proximal sheath 440 is along the outer curve of the aorta, the angled distal edge 444 may allow one of the arches 101 along the inside curve (left coronary side)

to be released before the remaining arches, or all arches may be released simultaneously, depending on the angle of the angled distal edge 444 and the curvature of the anatomy. Alternatively, the angled distal edge 444 may be angled the same direction as the angled proximal edge 266 of the distal sheath 260. This orientation would allow the arch along the outer curve to be released first. Strategic shaping of the distal end of the proximal sheath may allow for better control of the release of the arches 101 which may improve final placement of the self-expanding stent-valve 100.

Figure 11:
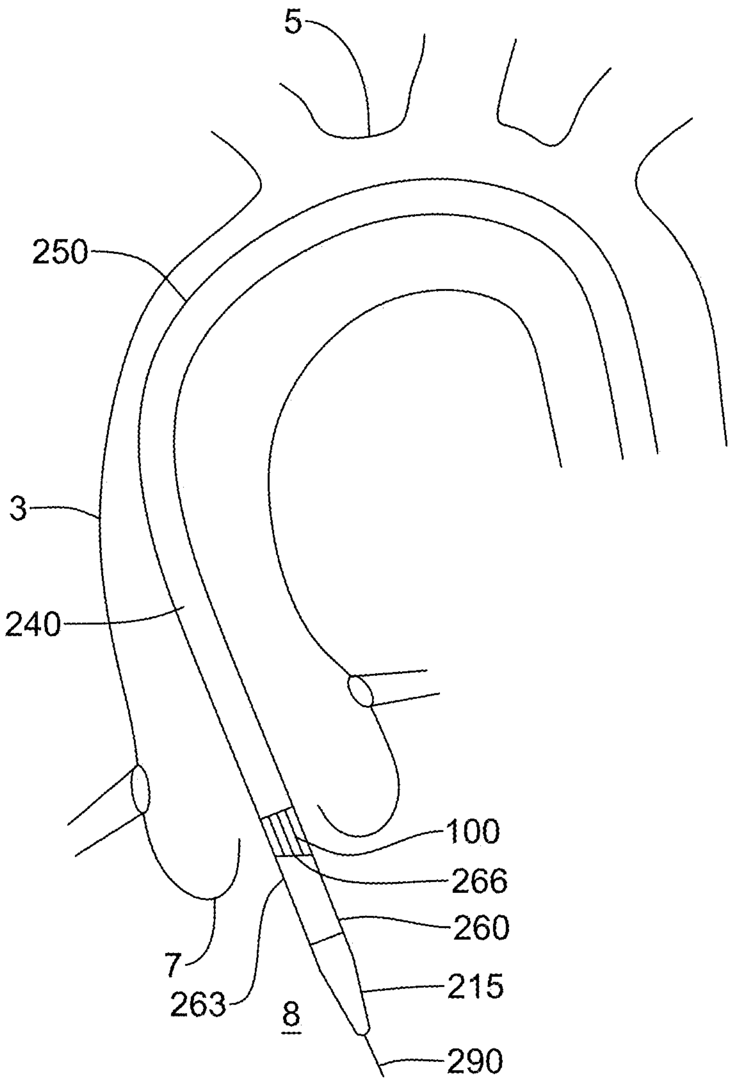
FIG. 11 illustrates the delivery system of FIG. 4 disposed within the aortic arch and aortic valve.

The delivery system in accordance with any of the above described embodiments may be used in a method to deliver a replacement stent-valve. In some embodiments, the stent-valve may be used to replace the aortic valve. A transfemoral approach may be used, in which the delivery system 250 may be tracked over a guidewire 290 previously placed through the femoral artery and vasculature, across the aortic arch 5 and through the aortic valve 7. The delivery system 250 may be advanced over the guidewire 290 until the distal tip 215 extends through the aortic valve 7, and into the left ventricle 8, as illustrated in FIG. 11. The radiopaque marker disposed along the long side 263 of the distal sheath 260 may be used to orient the distal shaft such that the long side 263 is aligned with the outer curve 3 of the aorta. With the delivery system positioned with the stent-valve 100 adjacent the aortic valve 7, the proximal sheath 240 may be withdrawn proximally. The distal sheath 260 remains in place to keep the lower portion of the stent constrained. As shown in FIG. 11, as the proximal sheath 240 is moved proximally, a portion of the stent-valve 100 is exposed, along with the angled proximal edge 266 of the distal sheath 260.

Figure 12:
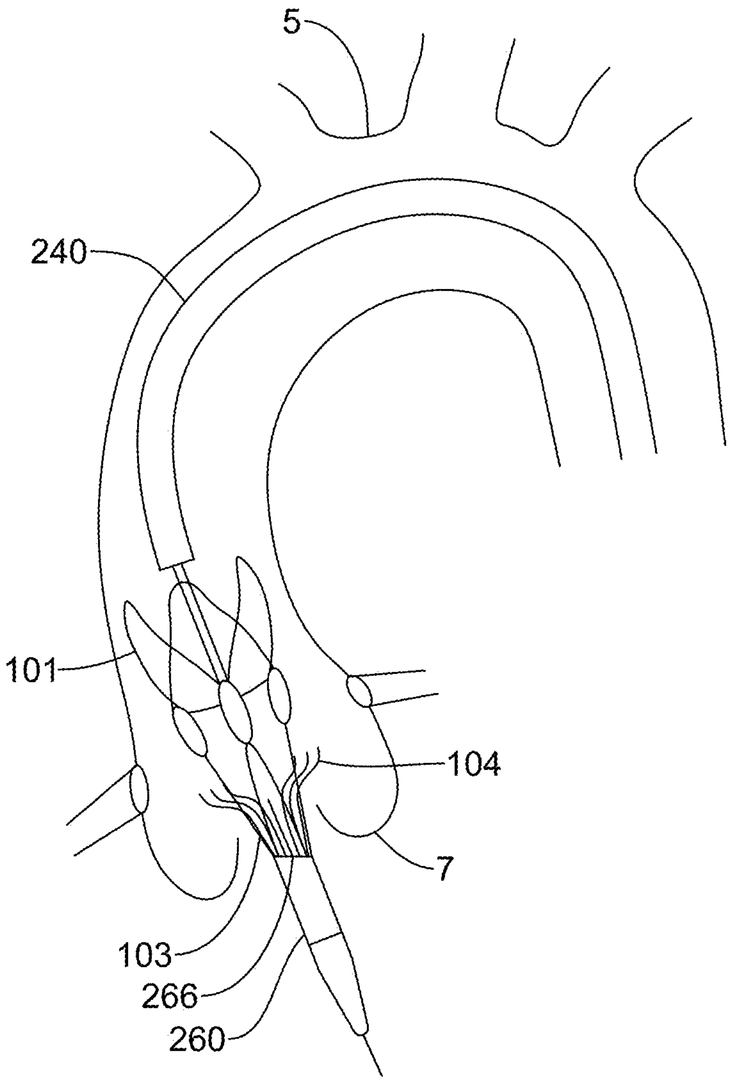
FIG. 12 illustrates the delivery system of FIG. 11 with the proximal sheath withdrawn from the stent-valve.
Figure 13:
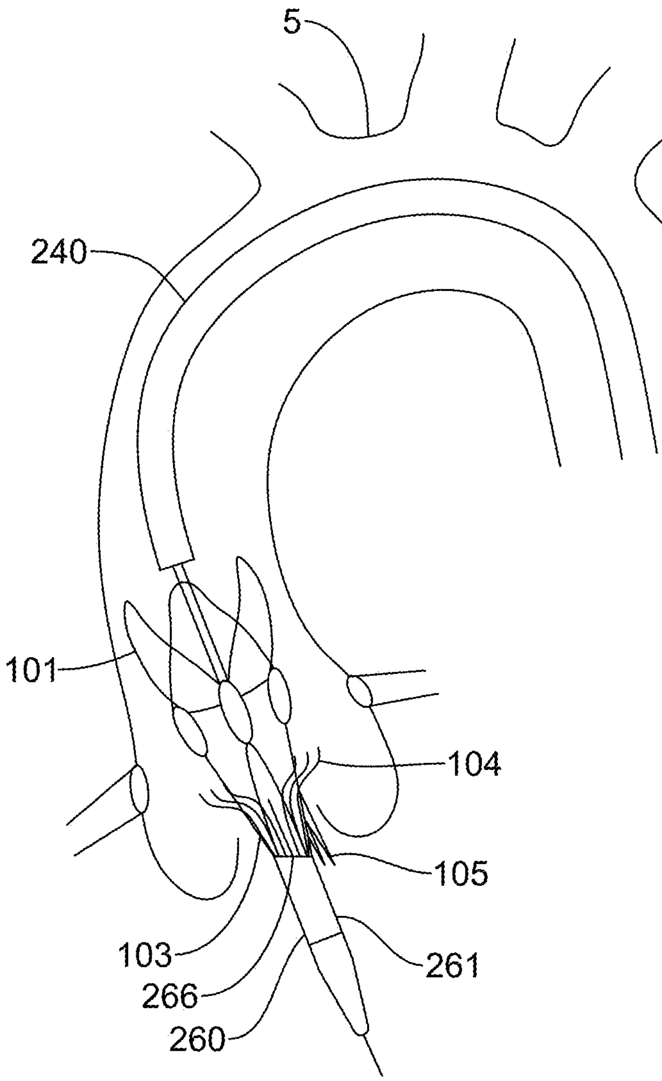
FIG. 13 illustrates the delivery system of FIG. 12 with the distal sheath partially withdrawn.
Figure 14:
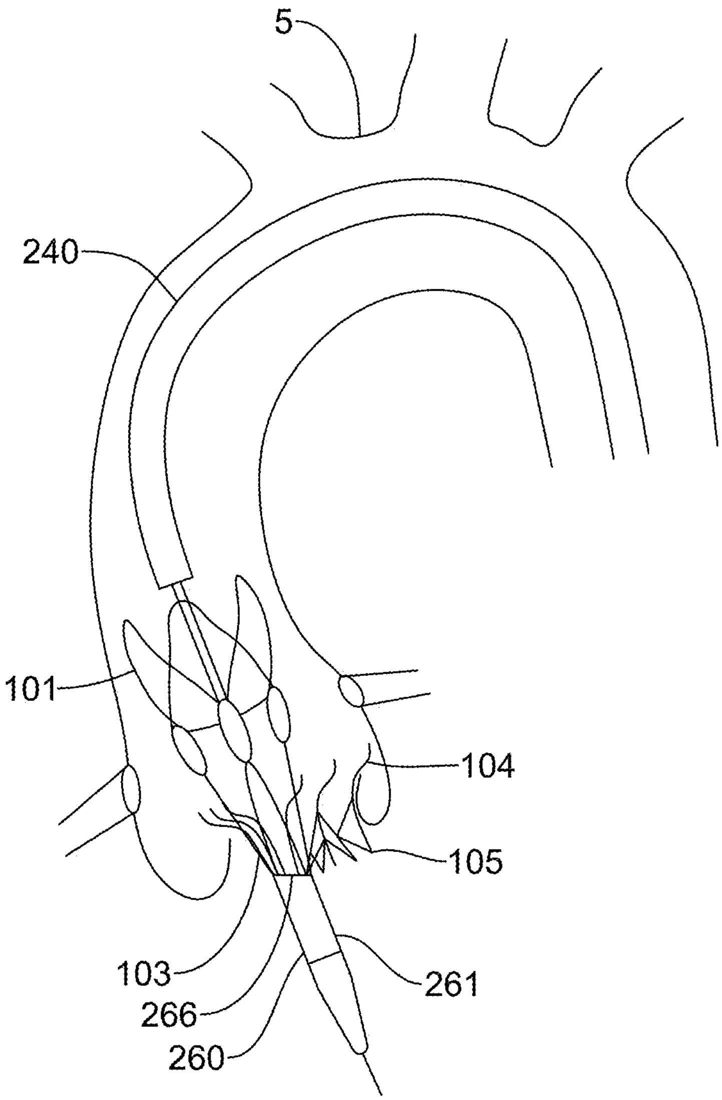
FIG. 14 illustrates the delivery system of FIG. 13 with the distal sheath withdrawn further.
Figure 15:
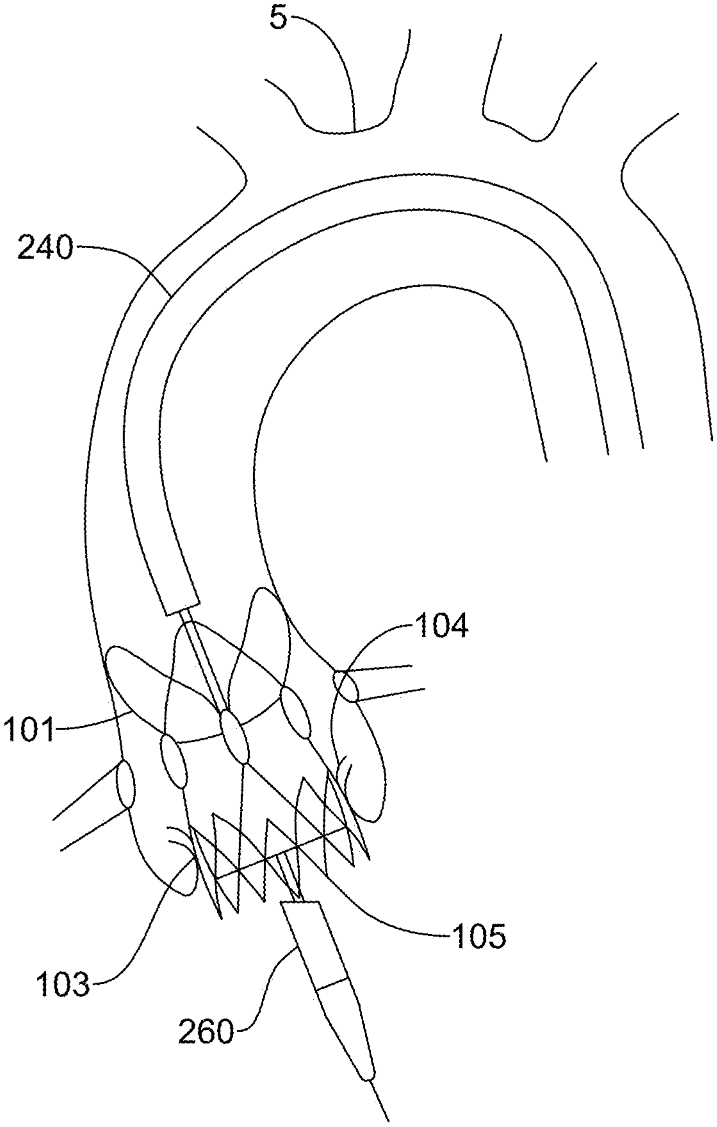
FIG. 15 illustrates the delivery system of FIG. 14 with the distal sheath fully withdrawn from the stent-valve.

The proximal sheath 240 may be withdrawn completely from the stent-valve, releasing the arches 101 and the upper anchoring crowns 104, as shown in FIG. 12. The distal sheath 260 remains over the lower stent portion 103, preventing it from expanding. At this point, the position of the stent-valve 100 may be adjusted relative to the aortic valve 7. In a first stage of deployment, the distal sheath 260 may then be moved distally off the lower stent portion 103 to a first position in which the angled proximal edge 266 releases lower crowns 105 incrementally from the short side 261 of the distal sheath 260 which corresponds with the inner curve of the aorta, as shown in FIG. 13. The lower crowns 105 on the outer curve side remain constrained by the long side of the distal sheath 260. As the distal sheath 260 is moved further distally, the released lower crowns 105 on the inner curve may be allowed to engage a desired portion of the anatomy, positioning the stent-valve for proper final deployment, as shown in FIG. 14. The release of lower crowns 105 on the inner curve does not create the same issues as release of lower crowns on the outer curve discussed above with regard to FIG. 3, because the inner curve maintains some compression of the lower stent portion 103, and the angled proximal edge 266 on the distal sheath 260 provides additional control over the deployment of the lower crowns 105 on the outer curve. In a second stage of deployment, further distal movement of the distal sheath 260 releases all of the lower crowns 105, and the stent-valve fully expands, with the arches 101 and upper anchoring crowns 104 engaging the vessel walls and the lower stent portion 103 seated within the aortic valve 7, as shown in FIG. 15.

In other embodiments, particularly with a shallower angle to the angled proximal edge 266, for example 10 degrees, the stent-valve deployment may occur in a single stage, with distal movement the angled proximal edge 266 releasing all of the lower crowns 105 simultaneously. This embodiment may achieve symmetrical distal release of the stent-valve, as the shallow angle of the angled proximal edge 266, when curved to following the anatomical curve of the aorta, releases the entire lower stent portion 103 simultaneously. In this embodiment, the deployment would move from the configuration shown in FIG. 12 to that shown in FIG. 15.

The materials that can be used for the various components of the delivery system 250 (and/or other systems or components disclosed herein) and the various elements thereof disclosed herein may include those commonly associated with medical devices. For simplicity purposes, the following discussion makes reference to the delivery system 250 (and variations, systems or components disclosed herein). However, this is not intended to limit the devices and methods described herein, as the discussion may be applied to other elements, members, components, or devices disclosed herein.

In some embodiments, delivery system 250 (and variations, systems or components thereof disclosed herein) may be made from a metal, metal alloy, ceramics, zirconia, polymer (some examples of which are disclosed below), a metal-polymer composite, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; cobalt chromium alloys, titanium and its alloys, alumina, metals with diamond-like coatings (DLC) or titanium nitride coatings, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "super-elastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super-elastic plateau and/or flag region that may be seen with super-elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a super-elastic alloy, for example a super-elastic nitinol can be used to achieve desired properties.

In at least some embodiments, portions or all of the delivery system 250 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery system 250 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands may also be incorporated into the design of the delivery system 250 (and variations, systems or components thereof disclosed herein) to achieve the same result.

In some embodiments, portions of the delivery system 250 (and variations, systems or components thereof disclosed herein), may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, Elast-Eon® from AorTech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery system configured to deliver a stent-valve, the delivery system comprising:

an inner shaft including a distal tip;

a stent-valve crimped onto the inner shaft, the stent-valve including an upper portion, a lower portion, and a valve;

a distal sheath disposed over at least the lower portion of the stent-valve, the distal sheath having a distal end coupled to the distal tip and a proximal free end having an angled proximal edge defining a short side and a long side of the distal sheath; and a proximal sheath disposed over at least the upper portion of the stent-valve;

wherein the proximal sheath is actuatable independently from the distal sheath, and moveable proximally to release the upper portion of the stent-valve;

wherein the distal sheath is moveable distally to release the lower portion of the stent-valve, wherein the angled proximal edge releases a first side of the lower portion of the stent-valve before an opposite second side.

2. The delivery system of claim 1, wherein the angled proximal edge on the distal sheath is angled 10 degrees to 70 degrees relative to a transverse axis of the distal sheath.

3. The delivery system of claim 2, wherein the angled proximal edge has a 10-degree to 20-degree angle.

4. The delivery system of claim 1, further comprising a marker indicating a position of the long side of the distal sheath.

5. The delivery system of claim 4, wherein the marker is a radiopaque marker on the distal sheath along the long side.

6. The delivery system of claim 4, wherein the marker is a radiopaque marker on the lower portion of the stent-valve.

7. The delivery system of claim 1, wherein the lower portion of the stent-valve includes a plurality of lower crowns, wherein the long side includes a proximal extension configured to cover 1-5 of the lower crowns while the remaining lower crowns are released.

8. The delivery system of claim 1, wherein the proximal sheath has a distal free end with an angled distal edge, wherein when the proximal sheath is moved proximally, the angled distal edge releases a first side of the upper portion of the stent-valve before an opposite second side.

9. The delivery system of claim 1, wherein the upper portion of the stent-valve includes a plurality of arches and a plurality of upper crowns, wherein a distal end of the proximal sheath extends over the plurality of arches and the plurality of upper crowns.

10. The delivery system of claim 1, wherein the distal sheath includes a polymer sheath and a reinforcement coil, wherein the reinforcement coil extends from the distal end of the distal sheath to a position adjacent the angled proximal edge.

11. The delivery system of claim 10, wherein the distal sheath includes a braid disposed proximal of the reinforcement coil.

12. A delivery system configured to deliver a stent-valve, the delivery system comprising:
- an inner shaft including a distal tip;
- a stent-valve crimped onto the inner shaft, the stent-valve including a plurality of upper crowns, a plurality of lower crowns, and a valve;
- a distal sheath disposed over and constraining the lower crowns, the distal sheath having a distal end coupled to the distal tip and a proximal free end having an angled proximal edge angled 5 degrees to 70 degrees relative to a transverse axis of the distal sheath; and
- a proximal sheath disposed over the upper crowns of the stent-valve;
- wherein the proximal sheath is actuatable independently from the distal sheath, and moveable proximally to release the upper crowns of the stent-valve;
- wherein the distal sheath is moveable distally to release the lower crowns of the stent-valve, wherein the angled proximal edge releases the lower crowns incrementally from a first side to a second side of the stent-valve.

13. The delivery system of claim 12, wherein the angled proximal edge has a 10-degree to 20-degree angle.

14. The delivery system of claim 12, wherein the angled proximal edge of the distal sheath defines a long side and an opposing short side of the distal sheath, the delivery system further comprising a marker indicating a position of the long side of the distal sheath.

15. The delivery system of claim 14, wherein the marker is a radiopaque marker on the distal sheath along the long side.

16. The delivery system of claim 14, wherein the marker is a radiopaque marker on one of the lower crowns positioned under the long side of the distal sheath.

17. The delivery system of claim 14, wherein the long side includes a proximal extension configured to cover 1-5 of the lower crowns while the remaining lower crowns are released.

18. A method of delivering a stent-valve, comprising:
- inserting a distal tip of a stent-valve delivery system through a patient's aorta and aortic valve, the delivery system including:
  - an inner shaft including the distal tip;
  - a stent-valve crimped onto the inner shaft, the stent-valve including an upper portion, a lower portion, and a valve;
  - a distal sheath disposed over at least the lower portion of the stent-valve, the distal sheath having a distal end coupled to the distal tip and a proximal free end having an angled proximal edge defining a short side and a long side, the distal sheath including a radiopaque marker on the long side; and
  - a proximal sheath disposed over at least the upper portion of the stent-valve;
- aligning the radiopaque marker along an outer curve of the aorta;
- moving the proximal sheath proximally to release the upper portion of the stent-valve; and
- moving the distal sheath distally to release the lower portion of the stent-valve, the angled proximal edge releasing a first side of the lower portion of the stent-valve positioned on an inner curve of the aorta, before an opposite second side.

19. The method of claim 18, wherein moving the distal sheath includes a first stage in which the distal sheath is moved distally to a first position in which a first side of the lower portion of the stent-valve is released while a second side of the lower portion of the stent-valve remains constrained by the distal sheath, and a second stage in which the distal sheath is moved further distally until an entirety of the lower portion of the stent-valve is released from the distal sheath.

20. The method of claim 19, wherein after the first stage, the first side of the lower portion of the stent-valve is allowed to engage a desired portion of the patient's anatomy, and then the second stage is performed to fully release the stent-valve.

* * * * *